US012696903B1

(12) United States Patent
Alqahtani et al.

(10) Patent No.: US 12,696,903 B1
(45) Date of Patent: Aug. 4, 2026

(54) **ECO-FRIENDLY INSECTICIDAL AGENT AGAINST *Aphis gossypii*(GLOVER.) INSECT**

(71) Applicant: KING FAISAL UNIVERSITY, Hofouf (SA)

(72) Inventors: Nashi Khaled Alqahtani, Hofouf (SA); Hany Mohamed Abd El-Lateef Ahmed, Hofouf (SA); Othman A. Farghaly, Al Baha (SA); Antar A. Abdelhamid, Al Baha (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 19/567,795

(22) Filed: Mar. 16, 2026

(51) Int. Cl.
*A01N 47/40* (2006.01)
*A01P 7/04* (2006.01)
*C07D 239/22* (2006.01)

(52) U.S. Cl.
CPC ................ *A01N 47/40* (2013.01); *A01P 7/04* (2021.08); *C07D 239/22* (2013.01)

(58) Field of Classification Search
CPC .......... A01N 47/40; A01P 7/04; C07D 239/22
See application file for complete search history.

(56) References Cited

U.S. PATENT DOCUMENTS 5,719,146 A 2/1998 Shiokawa et al.

OTHER PUBLICATIONS

Drar, Ali M., et al. "Functionalized Pyrimidines: Synthesis, Characterization, Structure-activity relationship and insecticidal evaluation of some new Neonicotinoid analogues against Cotton aphid." Journal of the Indian Chemical Society (2025): 102147. (Year: 2025).*

Amer, et al., "New route for the synthesis of new cyanoimino- and cyanoaminopyrimidines", Mol Divers 21, 875-880 (2017), DOI: https://doi.org/10.1007/s11030-017-9762-7 (Abstract).

Moustafa, et al., "One-pot synthesis of 4-aryl 2-cyanoimino-3,4-dihydro-1H-pyrimidines and their reactions", Chem Heterocycl Comp 48, 613-619 (2012). DOI: https://doi.org/10.1007/s10593-012-1034-y (Abstract).

Gonçalves, et al., "Ethyl 4-(2-fluorophenyl)-6 methyl-2-thioxo-1-(p-tolyl)-1,2,3,4-tetrahydropyrimidine-5-carboxylate", Molbank, 2018, 2018(4), M1029; DOI: https://doi.org/10.3390/M1029.

* cited by examiner

*Primary Examiner* — Kamal A Saeed
*Assistant Examiner* — Quincy McKoy
(74) *Attorney, Agent, or Firm* — Nath, Goldberg & Meyer; Joshua B. Goldberg

(57) ABSTRACT

Synthesis of ethyl ethyl-4-[2-(4-chlorophenyl)ethenyl]-2-(cyanoimino)-6-oxohexahydropyrimidine-5-carboxylate and its use as an insecticidal agent.

18 Claims, 2 Drawing Sheets

ECO-FRIENDLY INSECTICIDAL AGENT AGAINST *Aphis gossypii*(GLOVER.) INSECT

BACKGROUND

1. Field

The present disclosure relates to insecticidal agents and, particularly, ethyl-4-[2-(4-chlorophenyl)ethenyl]-2-(cyanoimino)-6-oxohexahydropyrimidine-5-carboxylate as an insecticidal agent.

2. Description of the Related Art

Neonicotinoids are potent insecticides that work well against a wide range of agricultural pests. For many years, they have been used to effectively control aphid pests, which cause significant financial harm to crops. The growing resistance to conventional chemical pesticides has become a key driver in the development of new insecticidal agents.

Cotton aphid, *Aphis gossypii* (Glover.) (Hemipetra/order: Aphididae) is considered one of the most devastating insect pests of crops such as eggplant. The cotton aphid, *A. gossypii*, is one of the most significant sucking mouthpart insect pests in agriculture. It targets a wide range of hosts, including more than 320 plant species from roughly 46 families. The cotton aphid, *A. gossypii*, punctures the leaf tissue and feeds on the phloem of its host plants using its sucking mouth parts. Consequently, excretions from honeydew lead to growth of black sooty mold fungus. Severe infection from *A. gossypii* can decrease plant vitality and production, ultimately producing large losses in the crop. The cotton aphid not only causes direct harm but also spreads over fifty different plant viruses.

Thus, new insecticides and/or pesticides solving the aforementioned problems using green chemistry methods are desired.

SUMMARY

The present subject matter relates to neonicotinoide analogues which can be used as insecticidal compounds with distinct modes of action. In an embodiment, the neonicotinoide analogues can include ethyl-4-[2-(4-chlorophenyl) ethenyl]-2-(cyanoimino)-6-oxohexahydropyrimidine-5-carboxylate. As described herein, ethyl-4-[2-(4-chlorophenyl) ethenyl]-2-(cyanoimino)-6-oxohexahydropyrimidine-5-carboxylate was created via a one-pot, three-component reaction of cyanoguanidine with a mixture of diethyl malonate and 3-(4-chlorophenyl) acrylaldehyde. The chemical structure of the novel product was verified using elemental and spectral analysis. Under laboratory conditions, the ethyl-4-[2-(4-chlorophenyl)ethenyl]-2-(cyanoimino)-6-oxohexahydropyrimidine-5-carboxylate (1) compound was evaluated as an insecticidal agent against black bean and cotton aphids (*Aphis gossypii*) nymphs and adults. Bioassay experiments indicated that ethyl-4-[2-(4-chlorophenyl)ethenyl]-2-(cyanoimino)-6-oxohexahydropyrimidine-5-carboxylate (1) has good insecticidal activities against *A. gossypii*. Compared with a reference acetamiprid, having an $LC_{50}$=0.245 ppm, ethyl-4-[2-(4-chlorophenyl)ethenyl]-2-(cyanoimino)-6-oxohexahydropyrimidine-5-carboxylate (1), was found to have toxicological activity with $LC_{50}$ value of 0.561 ppm, against adults of aphids. As such, ethyl-4-[2-(4-chlorophenyl)ethenyl]-2-(cyanoimino)-6-oxohexahydropyrimidine-5-carboxylate (1), a neonicotinoid insecticide, can guard several crops from *A. gossypii.*

In an embodiment, the present subject matter relates to an insecticide compound having the formula:

I

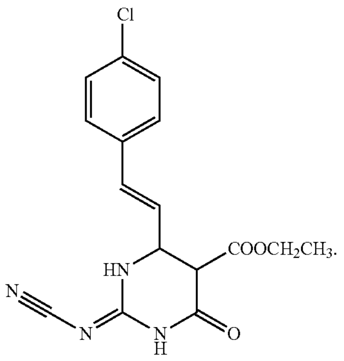

In another embodiment, the present subject matter relates to an insecticidally acceptable composition comprising an insecticidally effective amount of the insecticide compound and an insecticidally acceptable carrier.

In a further embodiment, the present subject matter relates to a method of killing insects comprising applying the insecticidally acceptable composition to a target site of insect infestation In an additional embodiment, the present subject matter relates to a method of repelling insects comprising applying the insecticidally acceptable composition to a target site of insect infestation.

In one more embodiment, the present subject matter relates to a method of controlling an insect pest comprising applying the insecticidally acceptable composition to a target site of insect infestation.

In a further embodiment, the present subject matter relates to a method of making ethyl-4-[2-(4-chlorophenyl)ethenyl]-2-(cyanoimino)-6-oxohexahydropyrimidine-5-carboxylate compound, the method comprising: combining cyanoguanidine and diethyl malonate and sodium ethoxide to obtain a reaction mixture; treating the reaction mixture with 3-(4-chlorophenyl) acrylaldehyde; and obtaining ethyl-4-[2-(4-chlorophenyl)ethenyl]-2-(cyanoimino)-6-oxohexahydropyrimidine-5-carboxylate.

These and other features of the present subject matter will become readily apparent upon further review of the following specification.

DETAILED DESCRIPTION OF THE PREFERRED EMBODIMENTS

Figure 1:
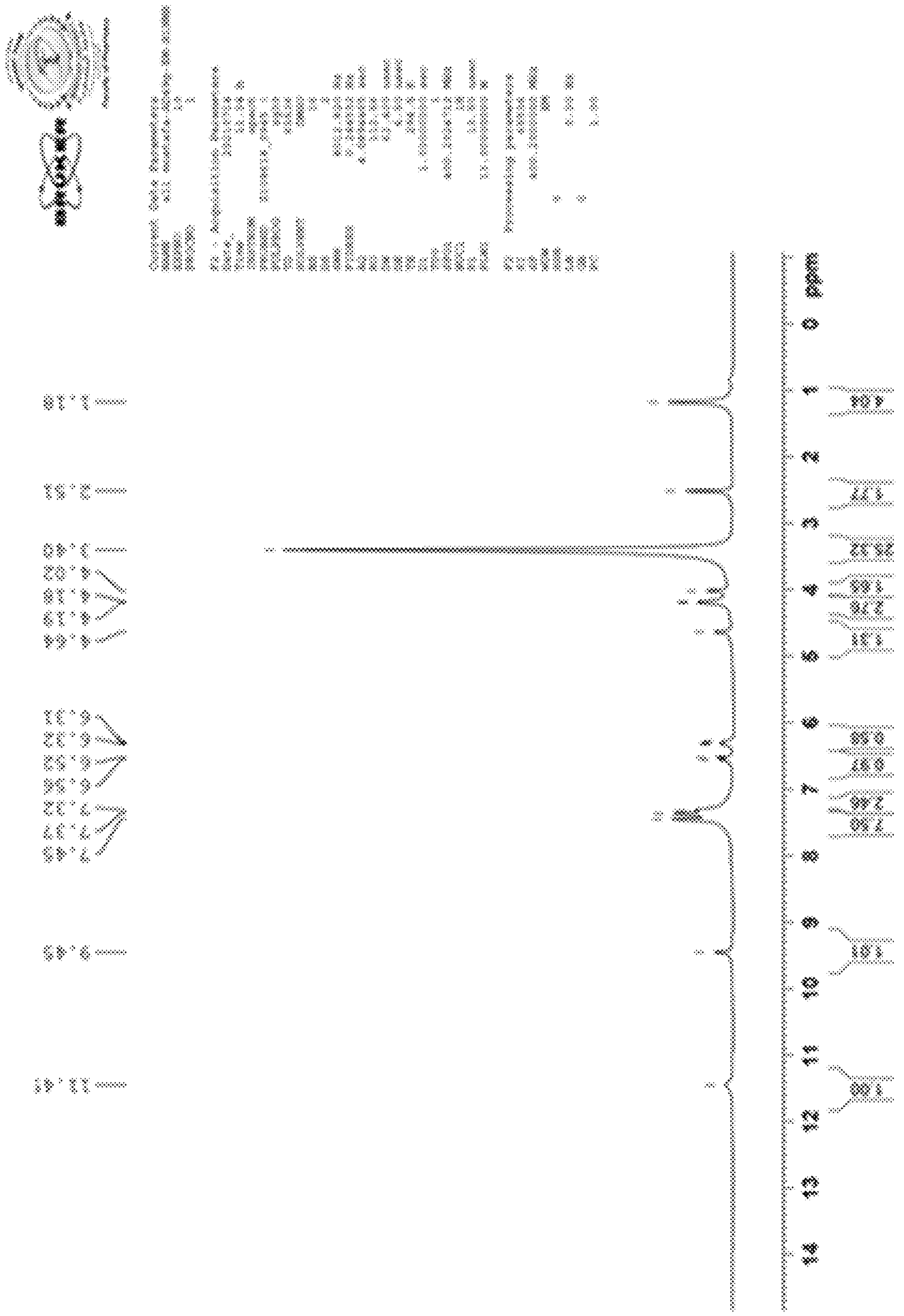
FIG. 1 is $^1$H-NMR spectrum of compound ethyl-4-[2-(4-chlorophenyl)ethenyl]-2-(cyanoimino)-6-oxohexahydropyrimidine-5-carboxylate.
Figure 2:
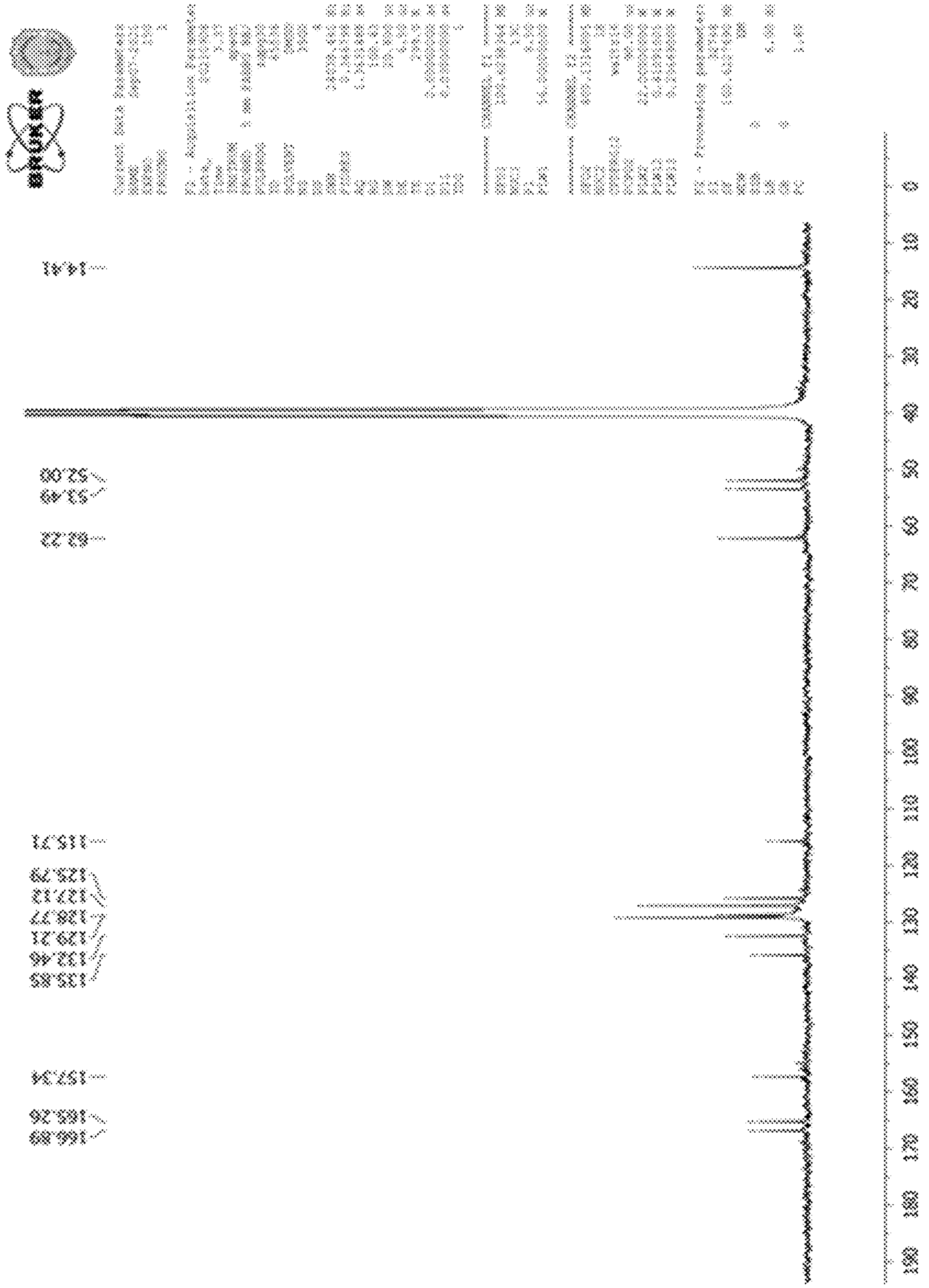
FIG. 2 is a $^{13}$C-NMR spectrum of compound ethyl-4-[2-(4-chlorophenyl)ethenyl]-2-(cyanoimino)-6-oxohexahydropyrimidine-5-carboxylate.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to neonicotinoid insecticides that can be used to protect several crops from destructive pests such as *A. gossypii.*

The present subject matter relates to a compound having the formula I:

I

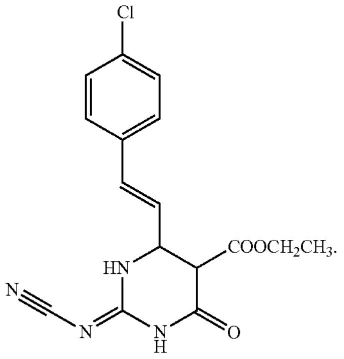

In an embodiment, the compound can be administered to a plant to kill or inhibit the growth of insects, such as insects belonging to the species *Aphis gossypii*. As set forth herein, the structure of the compound was confirmed by elemental and contemporary spectroscopic investigations (IR, UV, $^1$HNMR, $^{13}$CNMR, and elemental analysis). The insecticidal efficacy of the compound was checked against *Aphis gossypii*. under laboratory conditions and compared with acetamiprid as a reference insecticide. For compound I, an $LC_{50}$ of 0.561 was found against adult *Aphis gossypii*. For acetamiprid, a conventional insecticide, an $LC_{50}$ of 0.112 ppm was found against adult *Aphis gossypii.*

In an embodiment, the present subject matter relates to compositions including ethyl-4-[2-(4-chlorophenyl)ethenyl]-2-(cyanoimino)-6-oxohexahydropyrimidine-5-carboxylate (1) and an insecticidally acceptable carrier.

In certain embodiments, the ethyl-4-[2-(4-chlorophenyl) ethenyl]-2-(cyanoimino)-6-oxohexahydropyrimidine-5-carboxylate (1) compound can have a melting point of about 166° C. to about 168° C.

In another embodiment, the present subject matter relates to an insecticidally acceptable composition comprising an insecticidally effective amount of ethyl-4-[2-(4-chlorophenyl)ethenyl]-2-(cyanoimino)-6-oxohexahydropyrimidine-5-carboxylate (1) compound and an insecticidally acceptable carrier.

In some embodiments, the present compositions and methods of use can be used for combination treatment, where other insecticidal ingredients can be included therein, or can be co-administered therewith.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art.

The present compounds are typically administered at an insecticidally effective dosage, e.g., a dosage sufficient to provide a desired activity against insects.

While insecticidal dosages have yet to be optimized for the present compounds, generally, each treatment of the present composition could be expected to include from about 12.5 ppm to about 200 ppm, or mg/L, of the present compounds. In this regard, compositions having concentrations of the present compounds of about 200 ppm, about 100 ppm, about 50 ppm, about 25 ppm, or about 12.5 ppm, or mg/L, per application to a desired area of treatment are included within the present subject matter. The precise effective amount will vary from treatment to treatment and will depend upon the target area of application, the insect species being treated for, the number of insects present, and the like. The treatment area may be administered as many doses as is required to produce an effective treatment.

Liquid compositions can, for example, be prepared by dissolving, dispersing, etc. the active compound as defined above and optional adjuvants in a carrier, such as, for example, water, saline, aqueous dextrose, glycerol, glycols, ethanol, and the like, to thereby form a solution or suspension. If desired, the composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

In a further embodiment, the present subject matter relates to a method of killing insects comprising applying to said insects or to a target site of insect infestation an insecticidally effective amount of the insecticide compound and/or a composition including the same.

In an embodiment, the present methods of killing insects can include using an effective, eco-friendly agent for killing insects belonging to the *Aphis gossypii* (Glover) species. Accordingly, the present compound can be used as an insecticide to control populations of harmful insect pests, including, by way of non-limiting example, black bean aphids, cotton aphids, and aphids generally.

In another embodiment, the ethyl-4-[2-(4-chlorophenyl) ethenyl]-2-(cyanoimino)-6-oxohexahydropyrimidine-5-carboxylate compound can have an $LC_{50}$ of about 0.561 ppm against the species *Aphis gossypii* after 24 hours of treatment.

In an embodiment, the ethyl-4-[2-(4-chlorophenyl)ethenyl]-2-(cyanoimino)-6-oxohexahydropyrimidine-5-carboxylate compound can have an $LC_{50}$ of about 0.561 ppm against the species *Aphis gossypii* after 24 hours of treatment. In an embodiment, the ethyl-4-[2-(4-chlorophenyl) ethenyl]-2-(cyanoimino)-6-oxohexahydropyrimidine-5-carboxylate compound can have an $LC_{50}$ of about 0.112 ppm against nymphs of the species *Aphis gossypii* after 24 hours of treatment.

In a further embodiment of the present methods, the insect regulator compounds, ethyl-4-[2-(4-chlorophenyl)ethenyl]-2-(cyanoimino)-6-oxohexahydropyrimidine-5-carboxylate can be applied to insects directly.

In an additional embodiment, the present subject matter relates to a method of repelling insects comprising applying to a target site of insect infestation an insect repelling effective amount of the insect growth regulator compound and/or a composition including the same.

In an embodiment, the present methods of repelling insects can be effective against insects belonging to the *Aphis gossypii* species.

In one embodiment, the present subject matter relates to a method of controlling an insect pest comprising applying to a target site of insect infestation an insect controlling effective amount of the insecticide compound.

In an embodiment, the present methods of controlling insect pests can be effective against insects belonging to a species *Aphis gossypii.*

In a further embodiment, the present subject matter relates to a method of making the ethyl-4-[2-(4-chlorophenyl)ethenyl]-2-(cyanoimino)-6-oxohexahydropyrimidine-5-carboxylate compound, the method including: providing a reaction mixture including cyanoguanidine and diethyl malonate in ethanol, treating the reaction mixture with 3-(4-chlorophenyl) acrylaldehyde to obtain ethyl-4-[2-(4-chlorophenyl)ethenyl]-2-(cyanoimino)-6-oxohexahydropyrimidine-5-carboxylate. In an embodiment, the reaction mixture includes a catalytic amount of sodium ethoxide.

An exemplary synthesis method is provided in Scheme 1 below:

Scheme 1

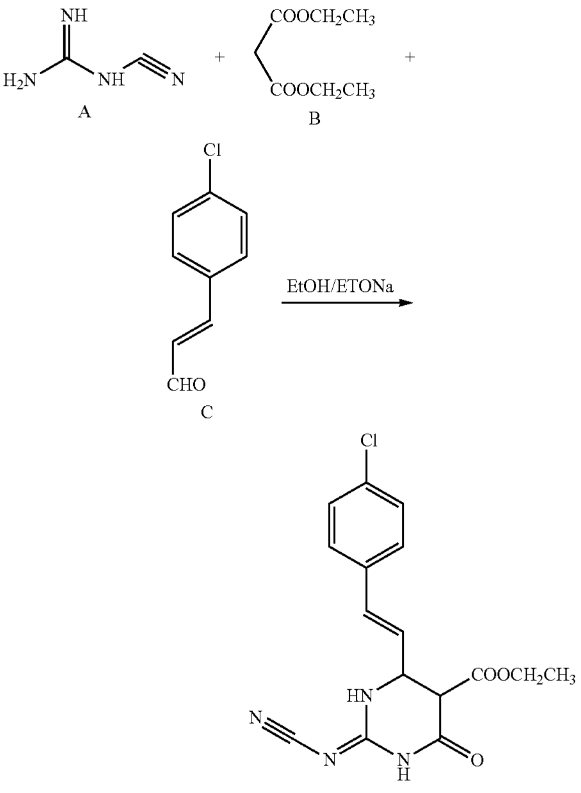

A B C 1

In an embodiment of the present production methods, ethyl-4-[2-(4-chlorophenyl)ethenyl]-2-(cyanoimino)-6-oxohexahydropyrimidine-5-carboxylate compound can be obtained in an about 62% yield.

In another embodiment, the ethyl-4-[2-(4-chlorophenyl) ethenyl]-2-(cyanoimino)-6-oxohexahydropyrimidine-5-carboxylate compound may have a melting point of about 166° C. to about 168° C.

In still other embodiments, the compound may be a white solid crystal.

In some embodiments, the diethyl malonate may be in ethanol as a solvent.

In additional embodiments, the sodium ethoxide may be added in a catalytic amount.

The following examples relate to various methods of synthesizing and using the compounds described herein. All compound numbers expressed herein are with reference to the synthetic pathway figures shown above.

EXAMPLES

Example 1

General Synthesis of ethyl-4-[2-(4-chlorophenyl) ethenyl]-2-(cyanoimino)-6-oxohexahydropyrimidine-5-carboxylate (1)

The compound was synthesized by using a one-pot three-component reaction technique. Cyanoguanidine (0.01 mole, 0.84 grams), and diethyl malonate (0.01 mole, 1.60 grams) in ethanol (40 mL) as a solvent in the presence of a catalytic amount of sodium ethoxide, was treated with, 3-(4-chlorophenyl) acrylaldehyde, to afford ethyl-4-[2-(4-chlorophenyl) ethenyl]-2-(cyanoimino)-6-oxohexahydropyrimidine-5-carboxylate (1).

Characterization data of Ethyl-4-[2-(4-chlorophenyl)ethenyl]-2-(cyanoimino)-6-oxohexahydropyrimidine-5-carboxylate (1):

White solid (62% yield), mp. 166-168° C.; IR (v, $cm^{-1}$): 3276 (N—H), 3176 (N—H), 3025 (CH arom.), 2982 (CH aliph.), 2186 (CN), 1737 (C—O ester), 1709 (C═O amid). $^1H$ NMR, (δ ppm): 11.45 (s, 1H, N—H exch.), 9.45 (s, 1H, N—H exch.) 7.45-7.32 (m, 4H, CH arom), 6.56-6.52 (d, 1H, CH═), 6.32-6.28 (d, 1H, CH═), 4.64-4.62 (d, 1H, CH), 4.19-4.12 (q, 2H, $CH_2$), 4.02-4.01 (d, 1H, N—CH), 1.20-1.16 (t, 3H, $CH_3$). $^{13}C$ NMR (δ ppm): 166.89, 165.26, 157.34, 135.58, 132.46, 129.21, 128.77, 127.12, 125.79, 115.71, 62.22, 53.49, 52.0, 14.41. Anal, for $C_{16}H_{15}ClN_4O_3$ (346.77) calcd/found: C: 55.42/55.31, H: 4.36/4.29, N: 16.16/16.08%.

Example 2

Insecticidal Bioassay Screening

Using the leaf dipping approach in a lab setting, ethyl-4-[2-(4-chlorophenyl)ethenyl]-2-(cyanoimino)-6-oxohexahydropyrimidine-5-carboxylate (1) was tested against Black bean aphids to demonstrate their insecticidal properties. Ethyl-4-[2-(4-chlorophenyl)ethenyl]-2-(cyanoimino)-6-oxohexahydropyrimidine-5-carboxylate (1) was dissolved in acetone, and a volume of water was added to reach the appropriate solution concentration. A surfactant of 0.1% Tween-80 was utilized (a control consisting solely of acetone, water, and 0.1% Tween-80). Twenty *A. gossypii* nymphs and twenty adults of about equal size were dipped for ten seconds in ethyl-4-[2-(4-chlorophenyl)ethenyl]-2-(cyanoimino)-6-oxohexahydropyrimidine-5-carboxylate (1) three times. For roughly 30 minutes, the tested insects were allowed to dry at room temperature. The toxicological experiments were conducted at a temperature of 25° C. and 5% relative humidity. The used pests were moved to glass jars with water once they had dried. Aphid mortality was measured using a binocular microscope 24 hours after treatment. Aphids that were immobile were deemed dead. Abbott's formula was used to examine the toxicity data of all produced pyrimidine derivatives. Probit analysis was used to estimate the $LC_{50}$ values, which are necessary for evaluating toxicological activity.

Abbott's formula:

$$\text{Corrected } \% = \left(1 - \frac{n \text{ in } T \text{ after treatment}}{n \text{ in } Co \text{ after treatment}}\right) * 100$$

Where: $n$ = Insect population, $T$ = treated, $Co$ = control

The results of the bioassay screening can be observed in Table 1, below.

TABLE 1

Toxicological activities of compound 1 towards the adults and nymphs of *A. gossypii*, after 24 hours of exposure.

| | Adults | | | Nymphs | | |
|---|---|---|---|---|---|---|
| | $LC_{50}$ (ppm) | Slope | Toxic ratio | $LC_{50}$ (ppm) | Slope | Toxic ratio |
| 1 | 0.561 | 0.566 ± 0.325 | 43.67 | 0.112 | 0.143 ± 0.312 | 44.64 |
| acetamiprid | 0.245 | 0.3248 ± 0.534 | 100 | 0.045 | 0.193 ± 0.306 | 100 |

Notes:
The Toxic ratio is calculated as the LC50 value of acetamiprid for baseline toxicity/the analogues' LC50 value X 100.

It is to be understood that the insecticide compounds, methods of making and using the same, and the compositions including the same, are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

I

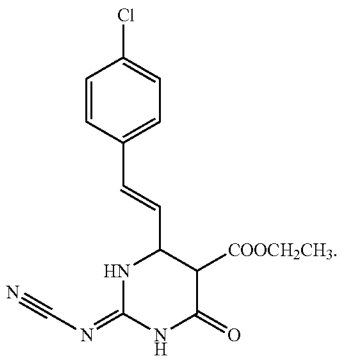

2. An insecticidally acceptable composition comprising an insecticidally effective amount of ethyl-4-[2-(4-chlorophenyl)ethenyl]-2-(cyanoimino)-6-oxohexahydropyrimidine-5-carboxylate compound having the formula I:

I

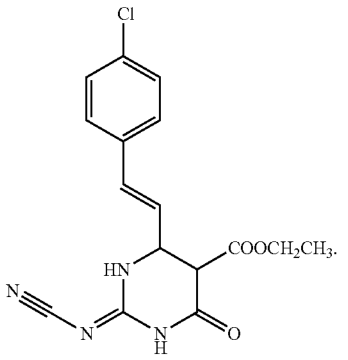

and an insecticidally acceptable carrier.

3. A method of killing insects comprising applying an insecticidally effective amount of the insecticidally acceptable composition of claim 2 to the insects or to a target site of insect infestation.

4. The method of killing insects of claim 3, wherein the insects belong to the species *Aphis gossypii.*

5. The method of killing insects of claim 4, wherein the ethyl-4-[2-(4-chlorophenyl)ethenyl]-2-(cyanoimino)-6-oxohexahydropyrimidine-5-carboxylate compound has an $LC_{50}$ of about 0.561 ppm against the species *Aphis gossypii* after 24 hours of treatment.

6. The method of killing insects of claim 4, wherein the ethyl-4-[2-(4-chlorophenyl)ethenyl]-2-(cyanoimino)-6-oxohexahydropyrimidine-5-carboxylate compound has an $LC_{50}$ of about 0.112 ppm against the species *Aphis gossypii* after 24 hours of treatment.

7. The method of killing insects of claim 3, wherein the ethyl-4-[2-(4-chlorophenyl)ethenyl]-2-(cyanoimino)-6-oxohexahydropyrimidine-5-carboxylate compound is applied to cotton leaves.

8. The method of killing insects of claim 3, wherein about 12.5 ppm to about 200 ppm of the insecticidally acceptable composition is applied to the insects or to the target site.

9. A method of repelling insects comprising applying to a target site of insect infestation an insecticidally effective amount of the insecticidally acceptable composition of claim 2.

10. The method of repelling insects of claim 9, wherein the insects belong to the species *Aphis gossypii.*

11. A method of controlling an insect pest, comprising applying to a target site of insect infestation an insecticidally effective amount of the insecticidally acceptable composition of claim 2.

12. The method of controlling the insect pest of claim 11, wherein the insect pest belongs to the species *Aphis gossypii.*

13. A method of making an ethyl-4-[2-(4-chlorophenyl)ethenyl]-2-(cyanoimino)-6-oxohexahydropyrimidine-5-carboxylate compound, the method comprising:

combining cyanoguanidine, diethyl malonate, and sodium ethoxide to obtain a reaction mixture;

treating the reaction mixture with 3-(4-chlorophenyl)acrylaldehyde to obtain ethyl-4-[2-(4-chlorophenyl)ethenyl]-2-(cyanoimino)-6-oxohexahydropyrimidine-5-carboxylate.

14. The method of making the ethyl-4-[2-(4-chlorophenyl)ethenyl]-2-(cyanoimino)-6-oxohexahydropyrimidine-5-carboxylate compound of claim 13, wherein the diethyl malonate is in ethanol.

15. The method of making the ethyl-4-[2-(4-chlorophenyl)ethenyl]-2-(cyanoimino)-6-oxohexahydropyrimidine-5-carboxylate compound of claim 14, wherein a catalytic amount of the sodium ethoxide is added.

16. The method of making the ethyl-4-[2-(4-chlorophenyl)ethenyl]-2-(cyanoimino)-6-oxohexahydropyrimidine-5-carboxylate compound of claim 14, wherein the ethyl-4-[2-(4-chlorophenyl)ethenyl]-2-(cyanoimino)-6-oxohexahydropyrimidine-5-carboxylate is obtained in about an 62% yield.

17. The method of making the ethyl-4-[2-(4-chlorophenyl)ethenyl]-2-(cyanoimino)-6-oxohexahydropyrimidine-5-carboxylate compound of claim 14, wherein the ethyl-4-[2-(4-chlorophenyl)ethenyl]-2-(cyanoimino)-6-oxohexahydropyrimidine-5-carboxylate has a melting point of at least about 166° C. to about 168° C.

18. The method of making the ethyl-4-[2-(4-chlorophenyl)ethenyl]-2-(cyanoimino)-6-oxohexahydropyrimidine-5-carboxylate compound of claim 14, wherein the ethyl-4-[2-(4-chlorophenyl)ethenyl]-2-(cyanoimino)-6-oxohexahydropyrimidine-5-carboxylate is a white solid.

* * * * *